(12) United States Patent
Kim

(10) Patent No.: US 7,806,821 B2
(45) Date of Patent: Oct. 5, 2010

(54) METHODS OF PHALLOPLASTY USING MULTIPLE SLITS TISSUE OR MULTIPLE PIECES TISSUE

(76) Inventor: Joon-Yong Kim, I-Park 301-603, Jeongja-dong, Bundang-gu, Gyeonggi-do (KR) 463-010

( * ) Notice: Subject to any disclaimer, the term of this patent is extended or adjusted under 35 U.S.C. 154(b) by 59 days.

(21) Appl. No.: 12/230,136

(22) Filed: Aug. 25, 2008

(65) Prior Publication Data

US 2010/0043807 A1    Feb. 25, 2010

(51) Int. Cl.
*A61F 5/00* (2006.01)
(52) U.S. Cl. .................................................. 600/38
(58) Field of Classification Search .............. 600/30, 600/38–41, 37; 128/898, 897
See application file for complete search history.

(56) References Cited

U.S. PATENT DOCUMENTS

| 5,921,246 | A * | 7/1999 | Cho | 128/898 |
| 6,582,356 | B2 * | 6/2003 | Kim | 600/40 |
| 7,070,558 | B2 * | 7/2006 | Gellman et al. | 600/37 |
| 2006/0096603 | A1 * | 5/2006 | Choi et al. | 128/898 |

* cited by examiner

*Primary Examiner*—Samuel G Gilbert
(74) *Attorney, Agent, or Firm*—The Nath Law Group; Joshua B. Goldberg; Mihsuhn Koh

(57) ABSTRACT

Disclosed herein is a method of phalloplasty for girth enhancement. It comprises incising minimally the outer skin of a penis; separating the skin and the hypoderm from a part immediately above Buck's fascia and peeling off the skin and the hypoderm in a region ranging from a part proximal to a glans to prepubic junction; forming a mesh structure of multiple slits in a penile implant; and fixing the penile implant to the penis by suture. The formation of a mesh structure of multiple slits or the use of an implant in multiple pieces makes it possible to cope with complications, thereby significantly reducing complications. Also, the multiple slits or multiple pieces form spaces therebetween, which lead to an increase in flexibility between the implant tissues, thereby enjoying the advantages of minimizing discomfort upon erection and reducing the occurrence of penis curvature. The delicate irregularities of the penis may serve as a factor promoting sexual stimulation upon sexual intercourse. Also, upon car-venosal injection therapy for erectile dysfunction, drugs for inducing erections can be easily injected into the space between the multiple slits or multiple pieces.

2 Claims, 4 Drawing Sheets

METHODS OF PHALLOPLASTY USING MULTIPLE SLITS TISSUE OR MULTIPLE PIECES TISSUE

BACKGROUND OF THE INVENTION

1. Field of the Invention

The present invention relates to methods of phalloplasty for girth enhancement. More particularly, the present invention relates to a method of phalloplasty for girth enhancement, using multiple slits implant or multiple pieces of an implant.

2. Description of the Related Art

In most surgery methods for penis enlargement, including girth enhancement and penis lengthening, a patient's penis is required to undergo a wide incision around the entire circumference area thereof or wide incision of the prepubic area thereof after being locally anesthetized. Conventionally, a synthetic material made from soft or liquid silicon or a biological tissue made from cartilage, fat, dermal fat or dermal tissue is used as a single implant having the same girth as the penis, so as to achieve penis enlargement.

Previously, and still often conducted these days, conventional phalloplasty has been widely performed with a silicon ring or silicon sheet because it is relatively inexpensive. However, silicon prostheses have not to be medicinally proven with regard to safety to the body. In addition, silicon grafts, in contrast to biological tissues, are accompanied by the sensation of foreign matter within the penile tissue. Further, complications of such artificial implants frequently occur. Nonetheless, phalloplasty for penis enlargement is even now widely performed with silicon because it is a relatively simple operation and the material cost is low.

Recently, autograft tissues, for example autologous dermal fat, or allograft tissue, for example human dermal tissue (Alloderm®), have been applied to phalloplasty for penis enlargement. Most phalloplasty methods require an autograft or allograft in the form of a single piece, or use it in such a manner as to encompass the entire area of the penis. Thus, a large amount of autografts or allografts are needed in order to perform the penis enlargement. In addition, when inflammation or necrosis occurs even at partial part of the implanted tissue, the entire implant must be removed because it is in the form of a single piece. On the whole, recovery from the transplant operation proceeds at a slow pace if it is large in size.

Conventional penis enlargement surgery, in which a patient's penis is widely incised around the entire area thereof, or the pubic area is incised, the wide incision takes a long period of time to be conducted. Furthermore, such wide incision leaves an extensive scar on the surface of the penis after the surgery, which is unsatisfactory to the patient, who wants a natural result and rapid convalescence.

In U.S. Published Patent Application No. 20060096603 a method for complex phalloplasty with minimal incision is taught, by which the penis immediately below the glans is incised to a length of 2-3 cm in a transverse direction. This method suffers from the disadvantage of requiring the removal of the entire penile prosthesis implanted in the penis when inflammation or necrosis occurs at only part of the transplantation site in the penis and necessitates a long period of time for convalescence.

SUMMARY OF THE INVENTION

Leading to the present invention, intensive and thorough research into novel complex phalloplasty, conducted by the present inventors, aiming at overcoming the problems encountered in the prior art, resulted in the finding that after being implanted to the penis, a transplant having multiple slits or comprising multiple pieces, whether an autograft, allograft or xenograft, provides the penis with spaces which make it possible to easily cope with concomitant consequences such as partial necrosis or inflammation of grafted implant and guarantee the flexibility of the penis upon erection.

It is therefore an object of the present invention to provide a method of penis enlargement surgery which is simple and economically favorable and makes it convenient to cope with consequences or complications.

In order to accomplish the above object, the present invention provides a method of phalloplasty for girth enhancement, comprising: incising the outer skin of a penis; separating the skin and the hypoderm from a part immediately above Buck's fascia and peeling off the skin and the hypoderm in a region ranging from Buck's fascia to a part proximal to a glans; forming a mesh structure of multiple slits in an implant; and fixing the implant against the penis by suturing.

Also provided for is a method further of phalloplasty for girth enhancement, comprising: incising minimally outer skin of a penis; separating skin and hypoderm from a part immediately above Buck's fascia and peeling off the skin and the hypoderm in a region ranging from a part proximal to a glans to prepubic junction; forming a mesh structure of multiple slits in a penile implant; and fixing the penile implant against the penis by suture.

In an embodiment, the methods may further comprise the step of dividing the implant into multiple pieces between the step of forming the multiple slits and the step of fixing the implant.

In another embodiment, the penile implant is selected from a group consisting of an autograft, an allograft and a xenograft.

BRIEF DESCRIPTION OF THE DRAWINGS

The above and other objects, features and other advantages of the present invention will be more clearly understood from the following detailed description taken in conjunction with the accompanying drawings, in which:

FIG. 1b is a view showing the application of a transplant tissue to the girth of the incised penis of FIG. 1a;

DESCRIPTION OF THE PREFERRED EMBODIMENTS

A detailed description is given of the present invention with reference to the drawings.

The present invention is directed to a method of phalloplasty for girth enhancement, using multiple slits tissue or multiple pieces of tissue rather than a single piece of intact tissue as a transplant.

The tissue for use in the method of phalloplasty according to the present invention may be autogenic, allogenic or xenogenic. An autograft tissue useful for penis enlargement is typically exemplified by autologous dermal fat. Human dermal tissue (for example, Alloderm®) and bovine collagen (for example, Lyoplant®) may typify the allograft tissue and the xenograft tissue useful for penis enlargement, respectively.

Figure 3:
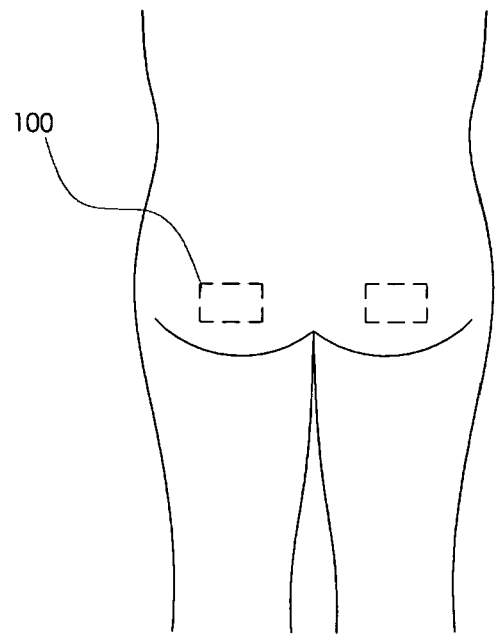
FIG. 3 is a view showing the preparation of an autologous tissue (100) from the hip of the patient himself.
Figure 4:
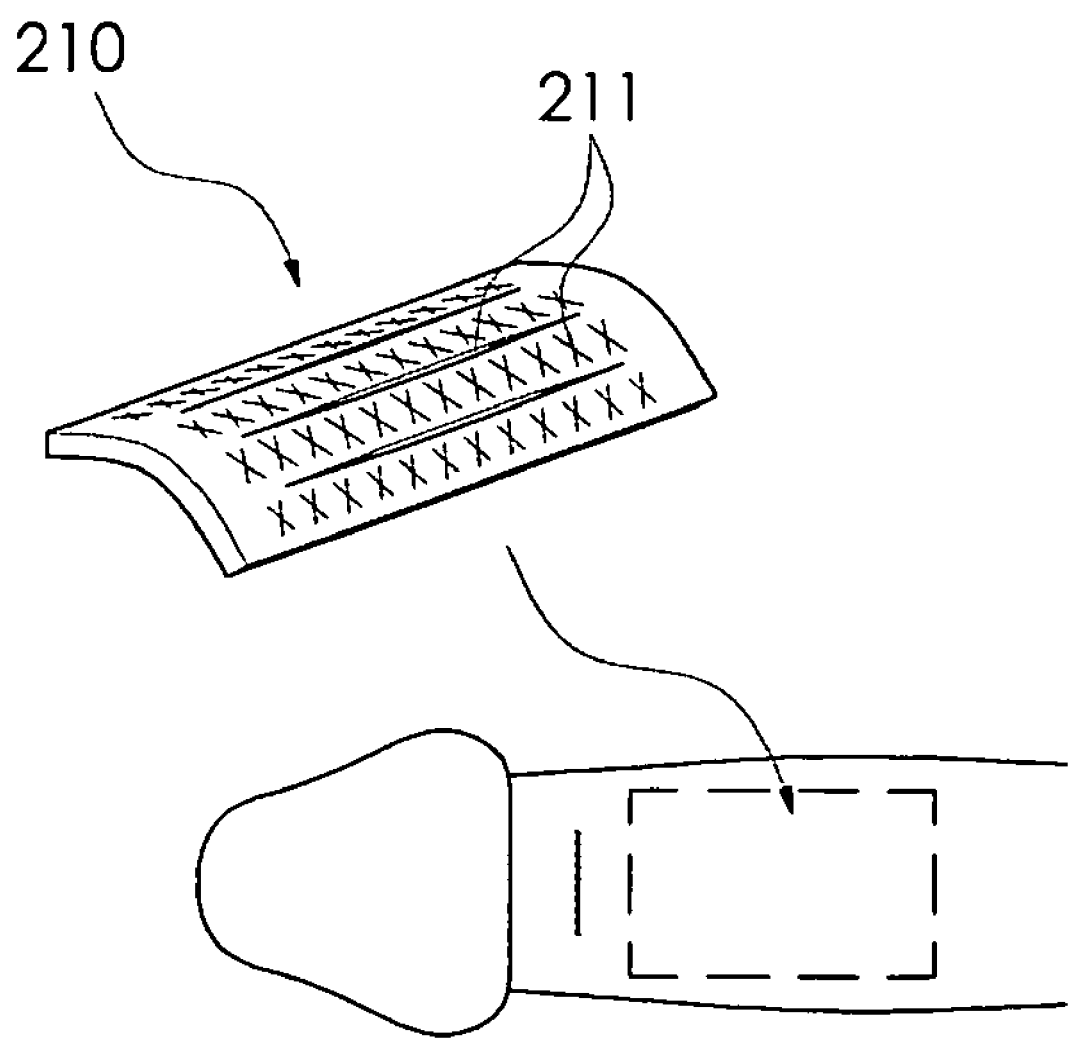
FIG. 4 is a view showing the application of the transplant tissue (210) with a mesh structure of multiple slits (211) formed therein to the penis by suturing.

An autogenic tissue useful in the method of phalloplasty according to the present invention may be prepared from the hip of the patient himself, as shown in FIG. 3.

In accordance with the present invention, the tissue preparation to be used as a transplant is partially incised in longitudinal and transverse directions so as to form a mesh structure of multiple slits therein.

Alternatively, the tissue preparation may be divided into many (3-7) pieces, which are together used as penile implants, after the formation of a mesh structure of multiple slits.

Figure 1A:
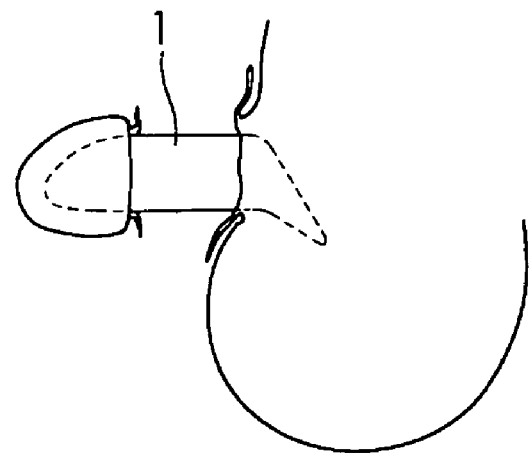
FIG. 1a is a view showing a penis (1) which is widely incised over the entire area thereof for conventional phalloplasty for penis enlargement.
Figure 1B:
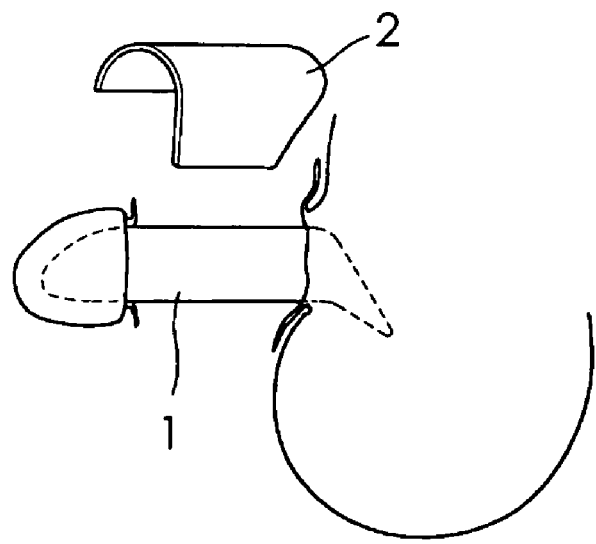
Figure 2:
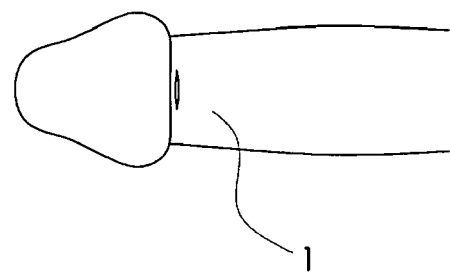
FIG. 2 is a view showing the penis (1) incised at a part immediately below the glans in a transverse direction in accordance with the method of phalloplasty of the present invention.

For the phalloplasty for penis enlargement according to the method of the present invention, then, as shown in FIG. 2, the penis is incised at a part immediately below the glans in a transverse direction.

Subsequently, the Buck's fascia and the dartos fascia are separated from the incised region to secure space for implantation of the tissue preparation.

The multiple slits implant is then applied to the space and fixed to the Buck's fascia with an absorbable suture.

Figure 5:
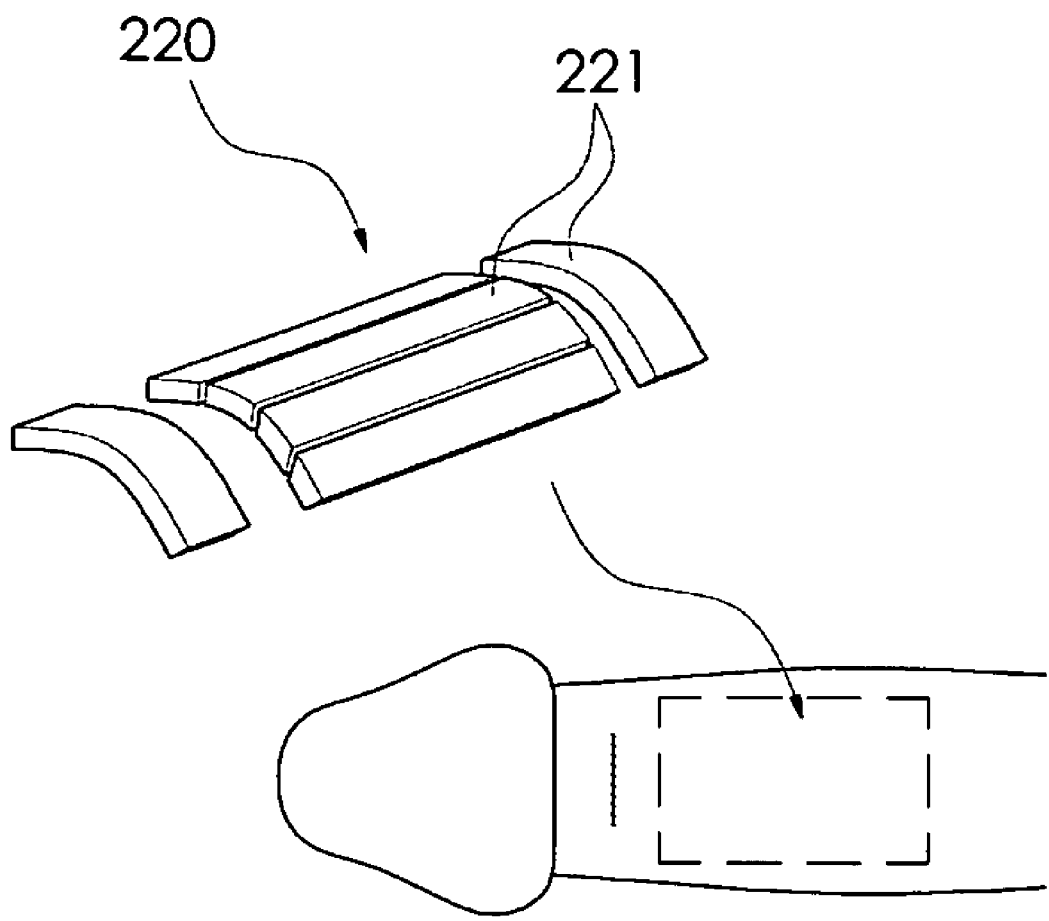
FIG. 5 is a view showing the application of multiple pieces (221) of a transplant tissue (220) to a glans zone, a distal zone and a proximal zone according to the method of phalloplasty of the present invention.

As for the multiple pieces implant, it is applied to many areas of the penis, including a glans zone, a distal zone and a proximal zone, as seen in FIG. 5.

The use of a multiple slits tissue or multiple pieces of tissue rather than a single piece of intact tissue as a transplant, the method of phalloplasty for penis enlargement, particularly girth enhancement, according to the present invention can widen or increase the circumference of the penis as much as possible. The size of the implant used in the present invention is smaller than that of the implant required by conventional methods, thereby enjoying various advantages over the conventional methods. For example, blood circulation through the multiple slits site and the implant is inhibited less when the penis is grafted with a small-sized transplant than with a large-sized transplant. Thus, edema at the incised region and the grafted region is also reduced, which leads to a positive effect on transplantation success and a preventive effect on the occurrence of complications. In addition, the formation of a mesh structure of multiple slits or the use of an implant provided in multiple pieces makes it possible to cope with complications such as partial tissue necrosis or transplant rejection, thereby significantly reducing complications. For example, when transplant rejection occurs, only the corresponding region need be selectively removed, allowing rapid reconstruction in accordance with the method of phalloplasty of the present invention. In contrast, the entire implant of the conventional methods must be removed upon the occurrence of a problem in even a partial region. Furthermore, the multiple slits or multiple pieces form spaces therebetween, which lead to an increase in flexibility between the implant tissues, thereby providing the advantages of minimizing discomfort upon erection and reducing the occurrence of penis curvature.

Besides, the delicate irregularities of the penises operated for enlargement by the phalloplasty method of the present invention may serve as a factor promoting sexual stimulation upon sexual intercourse. Also, upon carvenosal injection therapy for erectile dysfunction, drugs for inducing erection can be easily injected into the space between the multiple slits or multiple pieces.

A better understanding of the present invention may be obtained through the following examples, which are set forth to illustrate, but are not to be construed as the limit of the present invention.

EXAMPLE 1

Preparation of Implant for Use in Penis Enlargement

An autologous dermal fat graft is illustrated FIG. 3. As seen, the hip, the hypogastrium or the sacral area was locally anesthetized with 2% lidocaine and excised to give an oval or lengthy hexagonal dermal fat preparation 7-10 cm long and 3-5 cm wide. After epidermis was removed therefrom, the preparation taken from the donor site was placed in a physiological normal saline containing an antibiotic. The autologous dermal fat tissue should not be thicker than 1 cm. The donor site was sutured.

As for an allograft or a xenograft, the size thereof was adjusted to the figure of the target penis before hydration in antibiotic-supplemented physiological normal saline for 20 minutes.

EXAMPLE 2

Surgery Method for Girth Enhancement Using Multiple Slits

After the local anesthetic 2% lidocaine was applied to a region of the penis-extending from the proximal zone to the distal zone, the distal zone was transversely incised and the skin and the hypoderm were peeled off in a region ranging from Buck's fascia to the proximal zone. For an autologous graft the dermis preparation was positioned in such a manner that its fat layer was directed toward Buck's fascia, and fixed to Buck's fascia using an absorbable suture. Then, the dermis tissue was incised to form a mesh structure of multiple slits therein. In the case where allograft or xenograft is used, an implant was incised in a longitudinal direction and a transverse direction to form a mesh structure of multiple slits therein, followed by fixing and suturing it as in the foregoing.

EXAMPLE 3

Surgery Method for Girth Enhancement Using Multiple Pieces

An implant preparation obtained as in Example 1 was incised to form a mesh structure which had multiple slits therein and was divided into 3-7 pieces. These multiple pieces were fixed to Buck's fascia and the hypoderm tissue was sutured.

Results

The present inventors applied the method according to the present invention for complex phalloplasty with 550 patients suffering from small penis syndrome during a period from June, 2005 to December 2006, who ranged in age from 20 to 58, with the majority of men in their thirties and forties. As a result of conducting the method in the same manner as described in Example 1, 2 or 3, the penises were measured to be increased in circumference by 2.8-6.8 cm (4.8 cm on average). While the penises enlarged by conventional phalloplasty showed severe gap between the glans and the penis shaft due to the implant inserted, the method of the present invention was found to afford minimal gap.

It took one to one and half hours to complete the method according to the present invention for autologous dermal fat graft, including the operation time period for dermis preparation and donor site suturing. The operation time period for the allograft or xenograft was measured to be 30-50 minutes.

The penises operated on for enlargement by the phalloplasty method of the present invention were found to undergo minimal complications and convalescence time periods, as compared to those operated on using conventional methods. The minimal incision by the phalloplasty method of the present invention resulted in a significant reduction in scarring, tissue necrosis, and infection. In addition to the minimal incision, the formation of a mesh structure of multiple slits or the use of an implant in multiple pieces makes it possible to cope with complications such as partial tissue necrosis or transplant rejection, thereby significantly reducing sequelae. Furthermore, the multiple slits or multiple pieces form spaces therebetween, which lead to an increase in flexibility between the implant tissues, thereby enjoying the advantages of minimizing discomfort upon erection and reducing the occurrence of penis curvature.

Besides, the delicate irregularities in the penises operated by the phalloplasty method of the present invention may serve as a factor promoting sexual stimulation upon sexual intercourse. Also, upon carvenosal injection therapy for erectile dysfunction, drugs for inducing erection can be easily injected into the space between the multiple slits or multiple pieces.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of phalloplasty for girth enhancement, comprising:
    incising minimally outer skin of a penis;
    separating skin and hypoderm from a part immediately above Bucks' fascia and peeling off the skin and the hypoderm in a region ranging from a part proximal to a glans to prepubic junction;
    forming a mesh structure and/or multiple slits on a penile implant, the penile implant comprising multiple pieces of implant; and
    fixing the penile implant against the penis by suture.

2. The method according to claim 1, wherein the penile implant is selected from a group consisting of an autograft, an allograft and a xenograft.

* * * * *